United States Patent
Weitzel et al.

[11] Patent Number: 5,563,298
[45] Date of Patent: Oct. 8, 1996

[54] STILBENE-BASED MATERIALS, THEIR PREPARATION AND USE

[75] Inventors: Hans-Peter Weitzel, Reischach; Horst Leigeber, Oberhaching; Peter Boldt; Jobst Leupold, both of Braunschweig, all of Germany

[73] Assignee: Consortium für elektrochemische Industrie GmbH, München, Germany

[21] Appl. No.: 388,395

[22] Filed: Feb. 14, 1995

[30] Foreign Application Priority Data

Feb. 18, 1994 [DE] Germany .......................... 44 05 220.0
Mar. 17, 1994 [DE] Germany .......................... 44 09 207.5

[51] Int. Cl.$^6$ .................................................. C07C 41/00
[52] U.S. Cl. ...................... 568/632; 568/634; 359/32
[58] Field of Search ......................... 568/632, 634; 359/632

[56] References Cited

U.S. PATENT DOCUMENTS

| | | |
|---|---|---|
| 4,410,570 | 10/1983 | Kreuzer et al. . |
| 4,807,968 | 2/1989 | Leslie ........................................ 350/311 |
| 5,185,419 | 2/1993 | Funk et al. ................................ 528/28 |
| 5,211,877 | 5/1993 | Andrejewski et al. . |
| 5,301,045 | 4/1994 | Miller et al. . |
| 5,359,439 | 10/1994 | Miller et al. . |

FOREIGN PATENT DOCUMENTS

| | | |
|---|---|---|
| 0442097 | 8/1991 | European Pat. Off. . |
| 2549798 | 5/1977 | Germany . |

OTHER PUBLICATIONS

Wang et al J. Org.Chem (1990) 55(16) 4846–9.
Macromolecules, vol. 26, No. 4, Feb. 15, 1993, Washington, pp. 659–667. M. O. Bautista et al., "Liquid Crystalline side chain polysiloxanes with 4–amino–4'–stibenecarboxylic ester mesogens".

Chemicals Abstracts, vol. 63, No. 5, Aug. 30, 1965, Columbus, OH, US, P. Aubrun "Derivatives of 2–Phenyl–1, 3–Indandione", Col. 5565; & Ann. Chim., vol. 9, No. 7–8, 1964, pp. 359–397.

*Primary Examiner*—Paul J. Killos
*Attorney, Agent, or Firm*—Collard & Roe, P.C.

[57] ABSTRACT

Materials of the formula I:

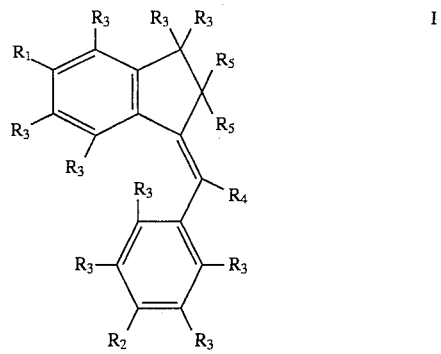

in which $R_1$, $R_2$ and $R_3$ in each case independently of one another can be identical or different and are a hydrogen atom, halogen atom, hydroxyl group, nitro group, cyano group or monovalent, optionally substituted organic radical; $R_4$ is a hydrogen atom, halogen atom, nitro group, cyano group or monovalent, optionally substituted organic radical; and $R_5$ can be identical or different and is a halogen atom, hydroxyl group, nitro group, cyano group or monovalent, optionally substituted organic radical.

8 Claims, No Drawings

STILBENE-BASED MATERIALS, THEIR PREPARATION AND USE

BACKGROUND OF THE INVENTION

1. Field of the Invention

The present invention relates to stilbene-based materials, their preparation and their use for the preparation of materials which can be structured by means of light.

2. The Prior Art

Examples of familiar materials which can be structured by light in the visible range are azo dyestuffs. Fields of use for such materials are, inter alia, information storage and optical elements which can be structured by means of light, such as, for example, holographic, optical elements.

Colored materials are unsuitable for various uses since the intrinsic color represents a limitation to the usable spectral range. Materials without absorption bands in the visible spectral range but with absorption bands in the UV or IR range are preferably used for colorless optical elements.

Merocyanines, fulgides and spiropyrans, for example, are used in the near infrared range. The known materials for optical elements which have absorption bands in the infrared range do not guarantee a high number of writing-erasing cycles since the dyestuffs are not stable in the long term (Fabian, Chem. Rev. 1992, 1197). Furthermore, many of these so-called infrared dyestuffs additionally have absorption bands at shorter wavelengths and therefore do not appear completely colorless.

Colorless devices can in principle also be realized by materials having absorption bands exclusively in the near UV range from 250 to 380 nm. Such devices have the advantage that information stored is not erased again by visible light. Furthermore, the storage density which can be achieved using light of shorter wavelength for writing in the information is significantly higher. However, the choice of dyestuffs is very limited here. Possible photochromic compounds here are primarily stilbenes. Stilbenoid compounds, however, have some side reactions which have already been known for a long time, such as, for example, cyclization to dihydrophenanthrene derivatives (with subsequent oxidation to phenanthrene) or dimerization to cyclobutanes. It has therefore not been possible to date for them to be used for optical information storage (L. Feringa, Tetrahedron, 1993, 8267–8310, H. Meier, Angewandte Chemie, Volume 31, No. 11, November 1992, pages 1399–1540).

SUMMARY OF THE INVENTION

It is an object of the present invention to provide stilbene-based materials which display no irreversible photochemical reactions.

It is another object of the present invention to provide polymers which comprise stilbene-based materials and can be structured by means of electromagnetic waves.

The above objects are achieved by materials of formula I:

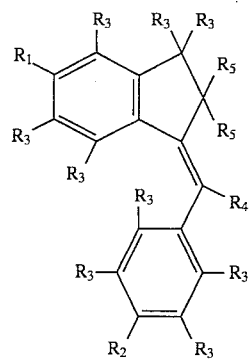

in which $R_1$, $R_2$ and $R_3$ in each case independently of one another can be identical or different and are a hydrogen atom, halogen atom, hydroxyl group, nitro group, cyano group or monovalent, optionally substituted organic radical, $R_4$ is a hydrogen atom, halogen atom, nitro group, cyano group or monovalent, optionally substituted organic radical, and $R_5$ can be identical or different and is a halogen atom, hydroxyl group, nitro group, cyano group or monovalent, optionally substituted organic radical.

The above-mentioned optionally substituted organic radicals are preferably hydrocarbon radicals having 1 to 18 carbon atoms, which are optionally substituted by halogen atoms, ether groups, ester groups, keto groups, epoxide groups or cyano groups.

Examples of such hydrocarbon radicals are alkyl radicals, such as the methyl, ethyl, n-propyl, iso-propyl, n-butyl, iso-butyl, tert-butyl, n-pentyl, iso-pentyl, neo-pentyl or tert-pentyl radical; hexyl radicals, such as the n-hexyl radical; heptyl radicals, such as the n-heptyl radical; octyl radicals, such as the n-octyl radical, and iso-octyl radicals, such as the 2,2,4-trimethylpentyl radical, nonyl radicals, such as the n-nonyl radical; decyl radicals, such as the n-decyl radical; dodecyl radicals, such as the n-dodecyl radical; octadecyl radicals, such as the n-octadecyl radical; alkenyl radicals, such as vinyl, butenyl, pentenyl, hexenyl, heptenyl, octenyl, octadienyl, decenyl, dodecenyl, hexadecenyl and the allyl radical; alkoxy radicals, such as the methoxy, ethoxy, n-propoxy, isopropoxy and n-, sec- and tert-butoxy radical and the pentoxy, hexoxy, octoxy, decoxy and hexadecoxy radical; alkenoxy radicals, such as the allyloxy radical and the butenyloxy, pentenyloxy, hexenyloxy, octenyloxy, decenyloxy and hexadecenyloxy radical; cycloalkyl radicals, such as cyclopentyl, cyclohexyl and cycloheptyl radicals and methylcyclohexyl radicals; cycloalkenyl radicals, such as cyclopentenyl, cyclohexenyl and cycloheptenyl radicals; cholestane radicals; the cholesteryl radical; fluorine, chlorine or bromine atoms; hydrogen atoms; hydroxyl, nitrile, (meth)acryloxy, (meth)acryloxyethylenoxy, (meth)acryloxydi(ethylenoxy), (meth)acryloxytri(ethylenoxy) and trimethylsilyl and triethylsilyl groups; aryl radicals, such as the phenyl, naphthyl, anthryl and phenanthryl radical; and alkaryl radicals, such as o-, m- and p-tolyl radicals, xylyl radicals and ethylphenyl radicals, and aralkyl radicals, such as the benzyl radical and the α- and the β-phenylethyl radical.

Examples of substituted hydrocarbon radicals are cyanoalkyl radicals, such as the β-cyanoethyl radical, and halogenated hydrocarbon radicals, for example haloalkyl radicals, such as the 3,3,3-trifluoro-n-propyl radical, the 2,2,2,2'2'2'-hexafluoroisopropyl radical and the heptafluoroisopropyl radical, and haloaryl radicals, such as the o-, m- and p-chlorophenyl radical.

Preferably, in formula I:
$R_1$, $R_2$ and $R_3$ in each case independently of one another are a hydrogen atom or alkyl, alkenyl, alkoxy or alkenoxy radical,
$R_4$, is a hydrogen atom or alkyl radical and
$R_5$, is an alkyl radical.

Particularly preferably, in formula I:
$R_1$ is an alkenoxy radical,
$R_2$ is a hydrogen atom or an alkyl or alkoxy radical,
$R_3$ is a hydrogen atom,
$R_4$ is a hydrogen atom and $R_5$ is a methyl radical.

The materials of the formula I according to the invention display neither dimerization nor cyclization such as occur with the known stilbene-based materials.

The only photochemical conversion to be observed is the desired cis/trans isomerization.

The materials according to the invention can be prepared by processes which are known per se, such as are described, for example, in J. March, Advanced Org. Chemistry, John Wiley & Son, 3rd edition, 1985, page 816, page 416.

Preferably, the materials according to the invention are prepared by alkylation of optionally substituted 1-indanones with alkyl halides, a subsequent Grignard reaction with optionally substituted benzylmagnesium halides and subsequent acid workup. The 1-indanones employed in the process according to the invention are preferably those of formula II

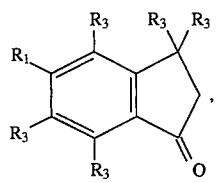

in which $R_1$ and $R_3$ have the meanings given for formula I.

Methyl-substituted 1-indanones or 5-alkoxy-substituted 1-indanones are preferably employed in the process according to the invention.

5-methoxy-1-indanone is particularly preferably employed.

The 1-indanones which can be employed in the process according to the invention are commercially obtainable or can be prepared by known processes, such as are described, for example, in J. March, Advanced Org. Chemistry, John Wiley & Son, 3rd edition, 1985, page 486.

The optionally substituted benzyl magnesium halides employed in the process according to the invention are preferably those of formula III

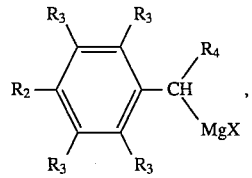

in which $R_2$, $R_3$ and $R_4$ have the meanings given for formula I.

Benzylmagnesium halides or 4-substituted benzylmagnesium halides are preferably employed in the process according to the invention.

Benzylmagnesium chloride or 4-alkoxybenzyl-magnesium chloride is particularly preferably employed.

The optionally substituted benzylmagnesium halides employed in the process according to the invention are commercially obtainable or can be prepared by known processes, such as are described, for example, in J. March, Advanced Org. Chemistry, John Wiley & Son, 3rd edition, 1985, page 816.

The alkylation of the optionally substituted 1-indanone is preferably carried out with alkyl halides in a suitable solvent, such as, for example, tert-butanol or tetrahydrofuran, 3 to 4 mol of alkyl halide and 1.0–1.1 mol of tert-butanol preferably being employed per mole of 1-indanone.

The reaction is preferably carried out at a temperature between 20° and 80° C. under atmospheric pressure. If appropriate, the substituents can also be modified to the particular desired extent in a manner which is known per se. It is thus possible, for example, to cleave ether substituents by treatment with $BBr_3$ (2 mol/mol of ether) in methylene chloride and to further derivatize the alcohol liberated.

The stilbene-based substances according to the invention are then prepared from the modified 1-indanone thus obtained by a Grignard reaction with an optionally modified benzylmagnesium halide. For this, 2 to 3 mol of optionally substituted benzylmagnesium halide are preferably employed per mole of modified 1-indanone. The reaction is preferably carried out at a temperature between 20° and 70° C. under normal pressure. The products according to the invention are obtained by subsequent acid workup to eliminate the alcohol primarily formed and purification by chromatography.

The products according to the invention can be separated into the isomers, if desired, by methods which are known per se, such as, for example, chromatographic processes.

The stilbene-based materials of the formula I according to the invention can be attached to any desired polymer backbones by replacement of one of the monovalent radicals $R_1$ to $R_5$ by a divalent organic radical.

The attachment is preferably effected by replacement of one of the monovalent radicals $R_1$ to $R_3$, particularly preferably the monovalent radical $R_1$, by a divalent organic radical.

It has been found, surprisingly, that such polymers can be structured particularly readily by electromagnetic waves.

The further object of the invention is therefore achieved by polymers which contain at least one stilbene radical of the formula I in which one of the monovalent radicals $R_1$ to $R_5$, preferably one of the radicals $R_1$ to $R_3$, particularly preferably the radical $R_1$, is replaced by a divalent organic radical.

The polymers according to the invention preferably have a polymer backbone which is built up from one or more of the monomers chosen from the group consisting of acrylates, methacrylates, vinyl ethers, vinyl esters, chloroacrylates, cyanoacrylates, styrenes, α-methylstyrene and/or from cyclic or linear polysiloxanes, to which the stilbene-based material of the formula I is attached as a side chain by replacement of one of the monovalent radicals $R_1$ to $R_5$ by a divalent organic radical $R_6$.

Examples of suitable divalent organic radicals $R_6$ are $C_1$ to $C_{18}$ alkylene or $C_1$ to $C_{18}$ alkoxylene groups.

$C_2$ to $C_5$ or $C_{11}$ alkylene or $C_2$ to $C_5$ or $C_{11}$ alkoxylene groups are particularly suitable divalent organic radicals.

The polymer backbone is preferably a side chain polymer having liquid crystal properties.

Suitable side chain polymers having liquid crystal properties are described, for example, in (Chem. Phys. Macromol; 1991, 211–271).

The polymer backbone is particularly preferably a cyclic polysiloxane having liquid crystal properties. Suitable cyclic polysiloxanes having liquid crystal properties are described, for example, in U.S. Pat. No. 5,211,877 and U.S. Pat. No. 4,410,570.

If appropriate, the polymer according to the invention can contain further mesogenic groups, such as, for example, derivatives of cyclohexane, such as cyclohexylcarboxylate, phenyl cyclohexanecarboxylate, cyclohexyl phenyl ether, cyclohexylbenzenes, dicyclohexyl derivatives, derivatives of stilbene, phenyl benzoate and its derivatives, steroids, such as cholesterol, derivatives thereof, such as cholesterol esters, cholestane and derivatives thereof, benzylideneanilines, azobenzene and its derivatives, azoxybenzene and derivatives thereof, alkyl and alkoxy derivatives of biphenyl, Schiff's bases, or non-mesogenic groups or photoreactive groups, such as, for example, azo groups.

The polymer backbone can be prepared by known processes such as are described, for example, in Makromol. Chem., Rapid Commun. 4, (1983), 795–799. Linkage of the stilbene derivative according to the invention is then carried out by means of processes which are known per se, such as are described, for example, in Poly. Bull. 1991, 27 (1), 37–40.

However, the polymer according to the invention can also be prepared by simultaneous polymerization of the polymer backbone and linkage of the stilbene derivative according to the invention. This can be carried out, for example, as described in H. Finkelmann, Thermotropic Liquid Crystals, editor G. W. Gray, Wiley Chichester CRAC Series Volume 22, Chapter 6, 1987, pages 145–170.

The choice of suitable polymer backbones and copolymer compositions allows the preparation of materials which can be structured by ultraviolet light.

Because they can readily be structured by means of electromagnetic waves, the polymers according to the invention are particularly suitable for the production of optical elements which can be structured. Such elements can be produced in a manner which is known per se, such as is described, for example, in DE 42 06 089 or DE 41 37 943.

The optical elements according to the invention are, for example, holographic optical elements, such as holographic screens, holographic lenses or holographic prisms. Such uses are described, for example, in Holographic Recording Materials, ed. H. M. Smith, Springer Verlag, 1977, Chapter 3.5, pages 97–99.

Other objects and features of the present invention will become apparent from the following detailed description considered in connection with the accompanying examples which discloses several embodiments of the present invention. It should be understood, however, that the examples are designed for the purpose of illustration only and not as a definition of the limits of the invention.

DETAILED DESCRIPTION OF PREFERRED EMBODIMENTS

EXAMPLE 1

Synthesis of 5-allyloxy-2,2,-dimethyl-1-(phenyl)methylene-indane a) 2,2-Dimethyl-5-methoxyindan-1-one 5 g (31 mmol) of 5-methoxyindan-1-one (Aldrich GmbH, Steinheim) and 17.5 g (123 mmol) of methyl iodide were dissolved in 100 ml of t-butanol under a nitrogen atmosphere. 13.8 g (123 mmol) of potassium t-butanolate were added in the course of 45 minutes. The reaction mixture thereby became brown in color. A white precipitate was formed. When the addition had ended, the mixture was heated at the boiling point under reflux for 1 hour. The cooled mixture was poured onto 300 ml of water and extracted twice with 50 ml of methylene chloride each time. After the extract had been dried over magnesium sulfate, the solvent was removed. The pale brown oily reaction product was obtained in a quantitative yield.

b) 2,2-Dimethyl-5-hydroxyindan-1-one 64 ml of a 1M $BBr_3$ solution in methylene chloride were added dropwise to a solution of 6.1 g (32 mmol) of the compound from a) in 100 ml of methylene chloride, while cooling with ice, and the mixture was stirred at room temperature for 96 hours. Thereafter, the dark brown reaction solution was poured onto 200 ml of water and extracted twice with 50 ml of ether each time. The ether phase was extracted twice by shaking with 1N sodium hydroxide solution. The alkaline aqueous phase was then acidified with dilute HCl (pH 1) and again extracted twice with 50 ml of ether each time. After filtration through silica gel, the ether was evaporated off on a rotary evaporator to give 4.6 g (26 mmol) of a pale beige solid.

c) 5-Allyloxy-2,2-dimethylindan-1-one 4.6 g (26 mmol) of compound b), 6.3 g (52 mmol) of allyl bromide and 14.4 g (103 mmol) of potassium carbonate were boiled under reflux in 200 ml of acetone for 2–3 hours. The conversion was monitored by thin layer chromatography. When the reaction had ended, the mixture was allowed to cool. The solid was then filtered off and washed with 50 ml of acetone. The two acetone filtrates were combined and the acetone was removed by means of a rotary evaporator. 5.5 g (25 mmol) of a pale brown oil were obtained.

d) 5-Allyloxy-2,2-dimethyl-1-(phenyl)methyleneindane

A solution of benzylmagnesium bromide was prepared by dropwise addition of 1 ml of bromine and then of 3.42 g (27 mmol) of benzyl chloride to 0.66 g (27 mmol) of magnesium turnings in 50 ml of dry ether and boiling under reflux for 1 hour. After cooling, a solution of 2 g (9.3 mmol) of compound c) in 50 ml of dry ether was added dropwise and the mixture was boiled under reflux for 2 hours. Ice was then added and the mixture was stirred for 30 minutes. Dilute hydrochloric acid was then added, while stirring, until the solid present had dissolved completely. The phases were separated and the aqueous phase was extracted twice with 50 ml of ether each time. The combined ether extracts were de-acidified with sodium bicarbonate solution (pH 7), washed with water and dried over sodium sulfate. The ether was then distilled off.

The pale yellow oily residue was dissolved in 200 ml of benzene and, after addition of 10 mg of p-toluenesulfonic acid, the mixture was heated at 90° C. for 4 hours. The cooled solution was filtered over silica gel and the benzene was distilled off under reduced pressure (15 mbar). The pale yellow crude product was dried under a high vacuum. Further purification was carried out by plate chromatography ($SiO_2$/petroleum ether). The product fraction ($R_f$=0.27) was eluted with methylene chloride. After removal of the methylene chloride by distillation, the product was dissolved again in 50 ml of petroleum ether and filtered through neutral aluminum oxide (activity level super I). The solvent was evaporated off on a rotary evaporator to give 2.54 g (8.8 mmol) of an almost colorless, oily product. This is a mixed product of cis and trans isomers of 5-allyloxy-2,2-dimethy-1-(phenyl) methyleneindane in a ratio of 10:1. The isomers were separated by means of column chromatography (aluminum oxide activity level super I/petroleum ether). The $R_f$ of the cis isomer was 0.21.

EXAMPLE 2

Copolymer D4H+ABdhchol, ABB and 5-allyloxy-2,2-dimethyl-1-(phenyl)methyleneindane 0.41 g (1.70 mmol) of tetramethylcyclotetrasiloxane- (D4H), 1.02 g (3.09 mmol) of $4^1$-(phenylphenyl) 4-(propen-2 -oxy)benzoate (ABB), 1.70 g (3.10 mmol) of dihydrocholesteryl 4 -(propen-2-oxy) benzoate (ABdhchol) and 0.20 g (0.69 mmol) of 5 -allyloxy-2,2-dimethyl-1-(phenyl)methyleneindane were dissolved in 10 ml of dry toluene and, after addition of 0.03 ml of a solution of dicyclopentadienylplatinum dichloride (1% by weight in methylene chloride), the mixture was heated at 100° C. for 1 hour.

When the reaction had ended, the catalyst was separated off over a short column packed with silica gel (1=3 cm, diameter=3 cm) and the product was precipitated in ethanol until the residual monomer content was less than 1%.

The end product was filtered over a 0.2 μm filter and dried at 90° C. in vacuo. 2.8 g (84%) of a substance having a reflection wavelength at 1130 nm were obtained. The substance has a cholesteric phase between the glass transition point at 50° C. and the clear point at 181° C.

EXAMPLE 3

Irradiation of 5-allyloxy-2,2-dimethyl-1-(phenyl)methyleneindane 0.352 mg of cis-5-allyloxy-2,2-dimethyl-1-(phenyl)methyleneindane was dissolved in methanol and the solution was diluted to 10 ml in a volumetric flask. This solution was irradiated with the light of an XeCl laser (λ=308 nm) in a quartz cell. After 10000 pulses (6 mJ/cm²) an NMR spectrum of this solution was measured. A content of the trans isomer of 13% was calculated from the spectrum. No signals for cyclization or dimerization products were observed.

EXAMPLE 4

Production of an optical element which can be structured

The substance from Example 2 was applied to a glass plate at 120° C. and covered with a second glass plate; a thin film of this substance between the glass plates was produced by shearing the glass plates. The sample was cooled to room temperature.

While only several embodiments of the present invention have been shown and described, it is to be understood that many changes and modifications may be made thereunto without departing from the spirit and scope of the invention as defined in the appended claims.

What is claimed is:
1. A process for the preparation of a material of the formula I:

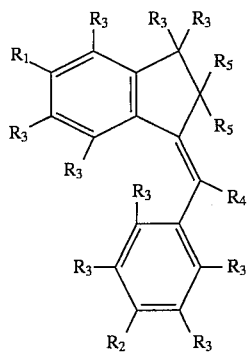

in which
$R_1$, $R_2$ and $R_3$ in each case independently of another can be identical or different and are a hydrogen atom, halogen atom, hydroxyl group, nitro group, cyano group or monovalent, optionally substituted organic radical, $R_4$ is a hydrogen atom, halogen atom, nitro group, cyano group or monovalent, optionally substituted organic radical and $R_5$ can be identical or different and is a halogen atom, hydroxyl group, nitro group, cyano group or monovalent, optionally substituted organic radical, which process comprises the steps of
alkylating an optionally substituted 1-indanone with an alkyl halide to produce an alkylated product;
subsequently reacting the alkylated product with an optionally substituted benzylmagnesium halide in a Grignard reaction to produce a further product; and
then subjecting the further product to acid workup.

2. A polymer which contains at least one stilbene material of the formula I:

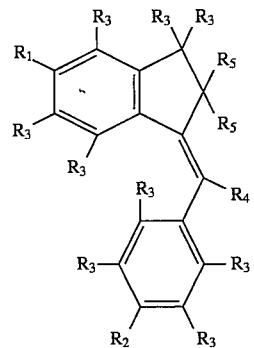

in which
$R_1$, $R_2$ and $R_3$ in each case independently of another can be identical or different and are a hydrogen atom, halogen atom, hydroxyl group, nitro group, cyano group or monovalent, optionally substituted organic radical, $R_4$ is a hydrogen atom, halogen atom, nitro group, cyano group or monovalent, optionally substituted organic radical and $R_5$ can be identical or different and is a halogen atom, hydroxyl group, nitro group, cyano group or monovalent, optionally substituted organic radical; and in which one of the monovalent radicals $R_1$ to $R_5$ is replaced by a divalent radical.

3. A polymer as claimed in claim 2, which is a side chain polymer having liquid crystal properties.

4. A polymer as claimed in claim 2, wherein said polymer has a polymer backbone which is built up from a cyclic and/or linear polysiloxane.

5. A polymer as claimed in claim 2, wherein the polymer has a backbone which is built up from one or more monomers selected from the group consisting of acrylate, methacrylate, chloroacrylate and cyanoacrylate.

6. A polymer as claimed in claim 2, wherein the polymer is built up from one or more monomers selected from the group consisting of vinyl ether, vinyl ester, styrene and α-methylstyrene.

7. An optical element comprising a material as claimed in claim 5.

8. An optical element comprising a polymer as claimed in claim 2.

* * * * *